United States Patent [19]

Naito et al.

[11] 4,232,155
[45] Nov. 4, 1980

[54] PURINE COMPOUNDS

[75] Inventors: Takayuki Naito, Kawasaki; Susumu Nakagawa, Tokyo; Tetsuro Yamasaki; Taka-Aki Okita, both of Ichikawa; Haruhiro Yamashita, Tokyo, all of Japan

[73] Assignee: Bristol-Myers Company, New York, N.Y.

[21] Appl. No.: 74,849

[22] Filed: Sep. 13, 1979

[51] Int. Cl.$^3$ ............................................. C07D 473/16
[52] U.S. Cl. ........................................ 544/277; 424/253
[58] Field of Search ............................................ 544/277

[56] References Cited

U.S. PATENT DOCUMENTS 4,172,829  10/1979  Naito et al. .......................... 424/253

FOREIGN PATENT DOCUMENTS 21593  7/1961  German Democratic Rep. ...... 544/277

OTHER PUBLICATIONS

Montgomery et al., J. Am. Chem. Soc., 80, 409–411 (1958).
Schaeffer et al., J. Am. Chem. Soc., 81, 197–201 (1959).

Primary Examiner—Paul M. Coughlan, Jr.
Attorney, Agent, or Firm—Robert H. Uloth; Robert E. Carnahan

[57] ABSTRACT

New orally active bronchodilating 6-amino-purine derivatives substituted in the two position with alkylamino or cyclohexylamino and in the nine position with 2-cyclohexenyl or cyclohexyl are disclosed.

5 Claims, No Drawings

PURINE COMPOUNDS

BACKGROUND OF THE INVENTION

This invention broadly relates to heterocyclic carbon compounds having drug and bio-affecting properties. More particularly, the invention concerns novel purine derivatives which have non-adrenergic smooth muscle relaxant properties making them particularly valuable in overcoming acute bronchospasm and as adjuncts in symptomatic management of chronic, obstructive pulmonary diseases (e.g., asthma, bronchitis, emphysema). It is also concerned with therapeutic methods and compositions employing one or more of the instant compounds as active ingredients.

Regarding types of non-adrenergic bronchodilators, the theophylline groups of xanthine derivatives are particularly prominent. For instance, aminophylline, the ethylenediamine salt of theophylline, is an effective bronchodilator which may be administered parenterally, orally, or rectally and is useful in patients where direct relaxation of bronchial muscle is desired. Notwithstanding widespread use, the xanthine class of non-adrenergic bronchodilators have major disadvantages with respect to gastric irritation, cardiovascular and central nervous system side effects. Thus, there is a need for new and effective bronchodilators which increased potency and/or fewer or reduced untoward effects. As shown by standard pharmacological tests, representative compounds of the instant invention have nonadrenergic bronchodilating activity with minimal cardiovascular and central nervous system side effects.

The basic purine nucleus contains a six-membered pyrimidine ring fused to the five-membered imidazole ring as shown in the following plane formula with the numbering system used herein noted.

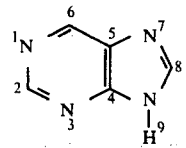

Various types of purine derivatives are known in which the parent purine is substituted at one or more of positions 2, 6, and 9 as illustrated in the following references.

1. J. A. Montgomery, et al., *J. Am. Chem. Soc.*, 80, 409–411 (1958) describe adenine derivatives of the formula

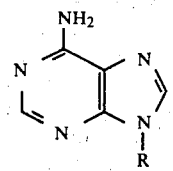

wherein R is n-butyl, cyclopentyl and cyclohexyl as potential anti-cancer agents.

2. H. J. Schaeffer, et al., *J. Am. Chem. Soc.*, 81, 197–201 (1959) describe synthesis of compounds having the formula

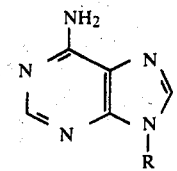

wherein R is 2-hydroxycyclohexyl or 2-cyclohexenyl as potential anti-cancer agents.

3. U.S. Pat. No. 3,917,837 (Lin, et al.) discloses the use of the compound

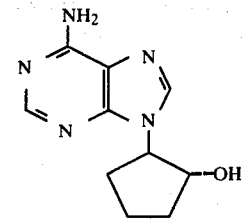

as an anti-inflammatory agent.

4. U.S. Pat. No. 3,862,189 (Schwender) concerns compounds of the formula

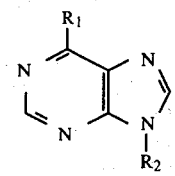

wherein, inter alia, $R_1$ is amino, alkylamino, aralkylamino, etc.; and $R_2$ is di-substituted phenylalkyl, tetrahydroquinoylalkyl, etc. useful as antianginal or bronchodilator agents.

5. U.S. Pat. No. 3,930,005 (Wojnar, et al.) discloses compounds of the formula

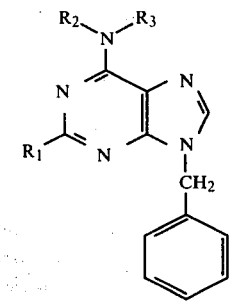

wherein $R_1$ is hydrogen, halogen, lower alkyl, lower alkoxy, amino, lower alkylamino or di-lower alkylamino and $R_2$ and $R_3$ may be hydrogen or lower alkyl as possessing anti-inflammatory activity.

6. R. Marumoto, et al., *Chem. Pharm. Bull.*, 23(4), 759–774 (1975) describe, inter alia, compounds of the formula

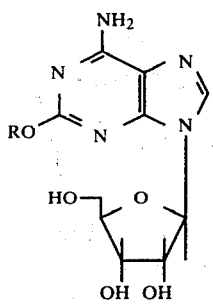

wherein R is (lower)alkyl. The compounds are said to have coronary vasodilating activity.

7. Belgian Pat. No. 853,086 (Farmdoc 70719Y) discloses compounds of the formula

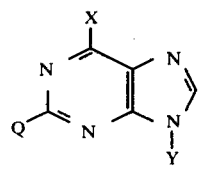

wherein *either* X is $C_1$-$C_6$ alkoxy or —NHR; R is H or (lower)alkyl; Y is $C_1$-$C_6$ alkyl, $C_3$-$C_{10}$ cycloalkyl or hydroxycycloalkyl, phenyl, halophenyl, trifluoromethyl-phenyl, bicycloalkyl or hydroxybicycloalkyl of up to 12 carbons, or —$AR^1$; A is methylene or ethylene; $R^1$ is phenyl, halophenyl, trifluoromethyl-phenyl, bicycloalkyl or hydroxybicycloalkyl of up to 12 carbons; Q is H, $C_1$-$C_6$ alkyl, $C_3$-$C_{10}$ cycloalkyl or hydroxycycloalkyl, bicycloalkyl or hydroxybicycloalkyl of up to 12 carbons, phenyl, halophenyl, trifluoromethyl-phenyl or $AR^1$; *or* X is halogen or (lower)dialkylamino; Y is methyl, ethyl, cyclopentyl, phenyl, halophenyl, trifluoromethyl-phenyl or benzyl and Q is as previously defined. The compounds are reported to be useful in treating psoriasis.

SUMMARY AND DETAILED DESCRIPTION OF THE INVENTION

The novel purine derivatives of the instant invention are characterized by a compound of Formula I

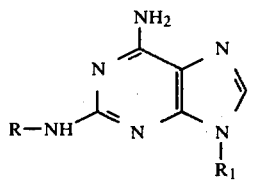

(I)

wherein R is lower alkyl of 1 to 4 carbon atoms or cyclohexyl; $R_1$ is cyclohexyl or 2-cyclohexenyl; or a pharmaceutically acceptable acid addition salt thereof. Said compounds effectively inhibit histamine induced bronchial construction by acting directly on tracheal muscle to relax spasm and in this respect belong to the non-adrenergic class of bronchodilators.

It is to be understood that the term "lower alkyl" contemplates both straight and branched chain groups containing from 1 to 4 carbon atoms inclusive. Illustrative of such groups are methyl, ethyl, propyl, isopropyl, 1-butyl, 1-methylpropyl, 2-methylpropyl, and tert.-butyl.

For the purpose of this disclosure, the term "pharmaceutically acceptable acid addition salt" denotes a salt form of a compound of Formula I obtained by combination with a non-toxic inorganic or organic acid which is relatively non-toxic in anionic form. Examples of non-toxic pharmaceutically acceptable acid addition salts of the compounds of Formula I are those formed with sulfuric, hydrochloric, phosphoric, hydrobromic, hydroiodic, sulfamic, methanesulfonic, benzenesulfonic, para-toluenesulfonic, acetic, lactic, succinic, malic, maleic, mucic, tartaric, citric, gluconic, benzoic, cinnamic, isethionic, fumaric, levulinic and related acids.

Conversion of Formula I compounds to corresponding nontoxic pharmaceutically acceptable acid addition salt is accomplished in conventional fashion by admixture of the base with at least one molecular equivalent of a selected acid in an inert organic solvent such as ethanol, benzene, ethyl acetate, ether, halogenated hydrocarbon and the like. Isolation of the salt is carried out by techniques known to the art such as inducing precipitation with a non-polar solvent (e.g. ether) in which the salt has limited solubility.

According to the present invention, compounds of Formula I are prepared by processes illustrated according to the following reaction scheme:

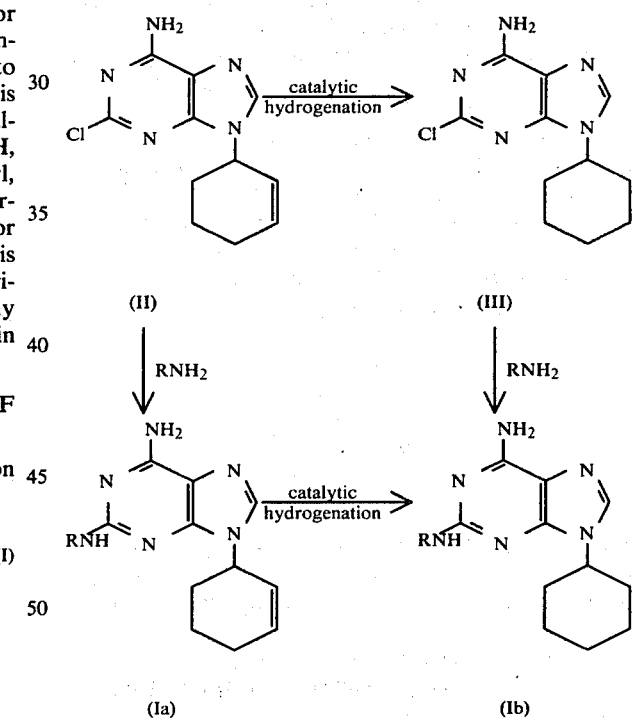

Compounds of Formula I are obtained by condensing 2-chloro-9-(2-cyclohexenyl)-9H-adenine (II) or 2-chloro-9-cyclohexyl-9H-adenine (III) with $RNH_2$ in reaction inert solvent, preferably a lower alkanol such as methanol or ethanol, to produce the desired free base product of Formula (Ia) or (Ib). The reaction is preferably carried out in a closed reaction vessel such as a sealed tube at elevated temperatures ranging from about 50° C. to 200° C.

Compounds of Formula (I) wherein $R_1$ is cyclohexyl (i.e. Ib) are also conveniently prepared by catalytic hydrogenation of the corresponding Ia products. For instance, a satisfactory procedure comprises hydrogenating a compound of Formula (Ia) in a non-reducible, inert solvent (e.g. methanol, ethanol, water, aqueous methanol, aqueous ethanol) using a conventional hydrogenation catalyst. Examples suitable catalysts include palladium black, Pd-BaSO$_4$, PtO$_2$, Ru-C, Rh-C, Raney nickel, CuCrO, RhCl[P(C$_6$H$_5$)$_3$]$_3$ and RuCl[P(C$_6$H$_5$)$_3$]$_3$. A preferred catalyst is palladium-on-carbon. Advantageous results have been achieved under conditions of room temperature and atmospheric pressure, although temperature and pressure are not critical for the hydrogenation step.

The requisite 2-chloro-9-(2-cyclohexenyl)-9H-adenine (II) and 2-chloro-9-cyclohexyl-9H-adenine (III) starting materials are obtained as described in allowed U.S. Patent application Ser. No. 904,146, U.S. Pat. No. 4,172,829, incorporated herein in its entirety by reference.

According to the present invention, compounds identified by Formula I and pharmaceutically acceptable salts thereof are useful in a process for eliciting a bronchodilating effect in a mammal in need thereof which comprises systemic administration to said mammal an effective dose of from about 0.1 to 20 mg./kg. body weight of the Formula I compound. A particularly preferred compound for carrying out the process is 2-n-propylamino-9-cyclohexyl-9H-adenine. It is intended by systemic administration to include both oral and parenteral routes, e.g., intramusclar, intravenous, intraperitoneal and subcutaneous. Also, the active ingredient may be given by inhalation employing a suitable aerosol preparation. Oral administration is preferred.

Another aspect the present invention provides a pharmaceutical composition in dosage unit form useful for relief of bronchial constriction in mammals. The composition comprises, as the active ingredient, an effective bronchodilating amount of a compound of Formula I or a pharmaceutically acceptable acid addition salt thereof, in admixture with a pharmaceutically acceptable carrier or diluent.

The pharmacologically active compounds of the present invention may be administered either as individual therapeutic agents or as mixtures with other therapeutic agents. They may be administered alone, but are generally given in the form of pharmaceutical compositions. Examples of such compositions include tablets, lozenges, capsules, powders, aerosol sprays, aqueous or oily suspensions, syrups, elixirs, and aqueous solutions.

The nature of the pharmaceutical composition and the pharmaceutical carrier or diluent will, of course, depend on the desired route of administration. For example, oral compositions may be in form of tablets or capsules and may contain conventional excipients such as binding agents (e.g. syrup, acacia, gelatin, sorbitol, tragacanth or polyvinylpyrrolidone), fillers (e.g. lactose, sugar, maize-starch, calcium phosphate, sorbitol or glycine), lubricants (e.g. magnesium stearate, talc, polyethylene glycol or silica), disintegrants (e.g. starch) or wetting agents (e.g. sodium lauryl sulfate). Oral liquid preparations may be in the form of aqueous or oily suspensions, solutions, emulsions, syrups, elixirs, etc. or may be presented as a dry product for reconstitution with water or other suitable vehicle before use. Such liquid preparations may contain conventional additives such as suspending agents, flavoring agents, diluents or emulsifying agents. For parenteral administration or inhalation, solutions or suspensions of a compound of Formula I with conventional pharmaceutical vehicles may be employed, e.g. as an aerosol spray for inhalation, as an aqueous solution for intravenous injection or as an oily suspension for intramuscular injection.

The compounds pharmaceutical compositions and broncho-dilating use thereof constituting embodiments of this invention are more fully illustrated by the following examples.

EXAMPLE 1

9-(2-Cyclohexenyl)-2-n-propylamino-9H-adenine

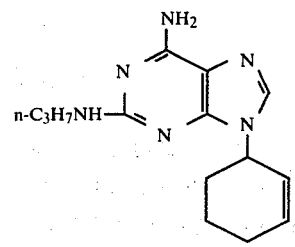

A mixture of 2-chloro-9-(2-cyclohexenyl)-9H-adenine (300 mg., 1.2 mmole) and 0.3 ml. of n-propylamine in 3 ml. of dry methanol is heated at 110° C. for 15 hrs. in a sealed tube and evaporated in vacuo to give an oil. The oil subjected to column chromatography on silica gel (20 g.) using chloroform-methanol as eluant affords an oil which on co-evaporation with ethyl acetate provides 282 mg. of 9-(2-cyclohexenyl)-2n-propylamino-9H-adenine, m.p. 73°–80° C. IR (KBr): 3300, 3150, 2920, 2860, 1630, 1600, 1535, 1490, 1470, 1405, 1360, 1200 cm$^{-1}$. UV: $\lambda_{max}^{EtOH}$ 259 nm($\epsilon$5,700), 290 nm($\epsilon$5,300). NMR (DMSO-d$_6$): $\delta$ 0.90(3H,t,J=4.5 Hz), 1.3–2.2(8H,m), 3.26(2H,t,J=6 Hz), 4.6–5.1(1H,m), 5.5–6.2(3H,m), 6.56(2H,s), 7.50(1H,s).

Anal. Calcd. for C$_{14}$H$_{20}$N$_6$: 1/10CH$_3$CO$_2$C$_2$H$_5$·$\frac{1}{2}$H$_2$O: C, 59.60; H, 7.59; N, 28.97. Found: C, 59.48; H, 7.16; N, 28.72.

EXAMPLE 2

9-(2-Cyclohexenyl)-2-cyclohexylamino-9H-adenine

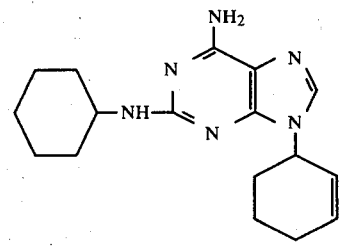

A mixture of 2-chloro-9-(2-cyclohexenyl)-9H-adenine (300 mg., 1.2 mmole) and 1 ml. of cyclohexylamine in 3 ml. of ethanol is heated at 120°–125° C. for a period of 89 hrs. in a sealed tube and then evaporated in vacuo to give an oil. Purification of residual oil by column chromatography on silica gel affords 288 mg (77%) of 9-(2-cyclohexenyl)-2-cyclohexylamino-9H-adenine, m.p. 108°–111° C. IR (KBr): 3315, 3170, 2925, 2845, 1630, 1600, 1530, 1470, 1405 cm$^{-1}$. UV: $\lambda_{max}^{EtOH}$ 224 nm($\epsilon$26,500), 259 nm($\epsilon$11,100), 291 nm($\epsilon$9,900). NMR(CDCl$_3$): $\delta$ 0.9–2.3(16H,m), 3.75(1H,br.s), 4.95(1H,br.s), 5.4–6.2(2H,m), 7.42(1H,s).

Anal. Calcd. for C$_{17}$H$_{24}$N$_6$: C, 65.36; H, 7.74; N, 26.90. Found: C, 65.40; H, 7.95; N, 26.71.

EXAMPLE 3

9-Cyclohexyl-2-n-propylamino-9H-adenine

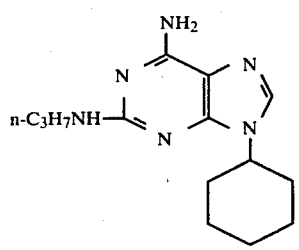

A solution of 9-(2-cyclohexyl)-2-n-propyllamino-9H-adenine (160 mg., 0.59 mmole) in 16 ml. of methanol is hydrogenated overnight with 160 mg. of 10% palladium-on-charcoal and filtered to remove catalyst. Concentration of the filtrate in vacuo affords 141 mg. (88%) of 9-cyclohexyl-2-n-propylamino-9H-adenine, m.p. 155°–156° C. IR (KBr): 3310, 3160, 2930, 2850, 1635, 1535, 1485, 1475, 1410 cm$^{-1}$. UV: $\lambda_{max}^{EtOH}$ 223 nm($\epsilon$24,100), 258.5 nm($\epsilon$8,800), 289.5 nm($\epsilon$8,400). NMR (DMSO-d$_6$):$\delta$0.89(3H,t,J=7.5 Hz), 1.1–2.2(12H,m), 3.13(2H,t,J=6 Hz), 3.7–4.4(1H,m), 6.06(1H,t,J=6 Hz), 6.52(2H,s), 7.19(1H,s).

Anal. Calcd. for $C_{14}H_{22}N_6 \cdot \frac{1}{2}H_2O$: C, 59.34; H, 8.18; N, 29.66. Found: C, 59.68; H, 7.98; N, 29.51.

EXAMPLE 4

9-Cyclohexyl-2-cyclohexylamino-9H-adenine

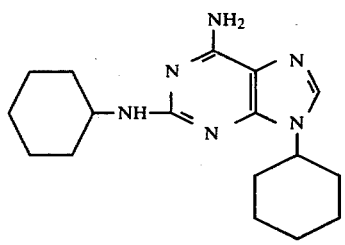

A solution of 9-(2-cyclohexenyl)-2-cyclohexylamino-9H-adenine (180 mg., 0.58 mmole) in 10 ml. of ethanol is hydrogenated overnight with 150 mg. of 10% palladium-on-charcoal and filtered. Concentration of the filtrate in vacuo yields 175 mg. (97%) of 9-cyclohexyl-2-cyclohexylamino-9H-adenine, m.p. 109°–117° C. IR (KBr): 3315, 3160, 2930, 2850, 1630, 1590, 1530, 1470, 1405 cm$^{-1}$. UV: $\lambda_{max}^{EtOH}$ 224 nm($\epsilon$25,600), 259 nm($\epsilon$10,100), 290.5 nm($\epsilon$9.100). NMR(CDCl$_3$): $\epsilon$ 0.9–2.4(20H,m), 3.43–4.9(2H,m), 7.42(1H,s).

Anal. Calcd. for $C_{17}H_{26}N_6 \cdot \frac{1}{2}C_2H_5OH$: C, 64.06; H, 8.66; N, 24.90. Found: C, 64.65; H, 8.59; H, 25.26.

EXAMPLE 5

9-Cyclohexyl-2-(2-butylamino)-9H-adenine

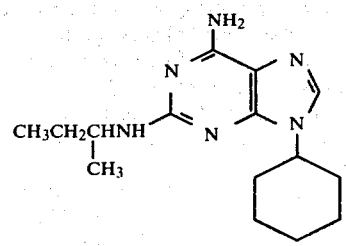

Reaction of 2-chloro-9-cyclohexyl-9H-adenine with sec.-butylamine according to the procedure of Example 1 affords the title compound.

EXAMPLE 6

Pharmacological Evaluation

A. In Vitro Bronchodilator Activity.

Tracheal chains of guinea pig were prepared by the method of A. Akcasu, Arch. Int. Pharmcodyn, Ther., 122, 201 (1959). The response to each test compound was recorded by the Magnus method and expressed as a percentage of the maximum response obtained with 0.1 mcg./ml. of isoproterenol prior to each experiment. Bronchodilator activity (in vitro) of aminophylline and test compounds of Examples 1–4 is expressed below as an EC$_{50}$ value (concentration in mcg./ml. which produces a relaxation which is 50% of the maximum response to 0.1 mcg./ml. of isoproterenol).

| In Vitro Test Results | |
|---|---|
| Compound of Example | EC$_{50}$ (mcg./ml.) |
| 1 | 0.47 |
| 2 | 0.24 |
| 3 | 0.75 |
| 4 | 0.21 |
| Aminophylline | 16.6 |

B. In Vivo Bronchodilator and Hypotensive Activity.

The in vivo bronchodilator activity of aminophylline and test compounds was evaluated according to a modification of the method described by L. G. W. James, J. Pharm. Pharmac., 21, 379 (1969) by measuring decrease in intratracheal pressure (ITP) in the guinea pig. The trachea of anesthetized guinea pig was cannulated and the ITP recorded on a polygraph under artificial ventilation. Arterial blood pressure (ABP; reflecting hypotensive activity) was also measured during the experiment. Either intravenous or intraduodenal routes of administration are used. Results set forth below express the bronchodilator activity (ITP) as an ED$_{50}$ value (dose in mg./kg. resulting in a 50% decrease in intratracheal pressure) and the hypotensive activity (ABP) as an ED$_{20}$ value (does in mg./kg. which reduces arterial blood pressure by 20%). The ratio of hypotensive ED$_{20}$/brochodilating ED$_{50}$ reflects an assessment of the separation of desirable brochodilator activity from undesirable cardiovascular (hypotensive) effect in the compounds. Those compounds exhibiting the largest ABP/ITP ratios have the greatest separation of bronchodilator activity and hypotensive side effect.

| Compound of Examples | Intravenous Test Results (mg./kg.) | | Ratio ABP/ITP |
|---|---|---|---|
| | ITP ED$_{50}$ | ABP ED$_{20}$ | |
| 1 | 1.4 | >3 | >2.1 |
| 2 | >3 | 2.4 | <0.8 |
| 3 | 0.49 | 2.8 | 5.7 |
| 4 | 1.5 | >3 | >2 |
| Aminophylline | 0.58 | 1.4 | 2.4 |

EXAMPLE 7

Pharmaceutical Compositions

A. Tablets.

The compounds of Formula I are compounded into tablets according to the following example:

| Materials | Amount |
|---|---|
| 9-Cyclohexyl-2-n-propylamino-9H-adenine | 20.0 g. |
| Magnesium stearate | 1.3 g. |
| Corn starch | 12.4 g. |
| Corn starch, pregelatinized | 1.3 g. |
| Lactose | 215.0 g. |

The foregoing materials are blended in a twin-shell blender and then granulated and pressed into tablets employing 250 mg. each. Each tablet contains about 20 mg. of active ingredient. The tablets may be scored and quartered so that unit doeses of 5.0 mg. of active ingredient may be conveniently obtained.

B. Capsules.

The compounds of Formula I are compounded into capsules according to the following example:

| Materials | Amount |
|---|---|
| 9-Cyclohexyl-2-n-propylamino-9H-adenine | 50.0 g. |
| Lactose | 221.0 g. |
| Magnesium stearate | 4.0 g. |

The foregoing materials are blended in a twin-shell blender and No. 1 hard gelatin capsules filled with 275 mg. of the blended composition. Each capsule contains 50 mg. of active ingredient.

What is claimed is:

1. A compound having Formula I

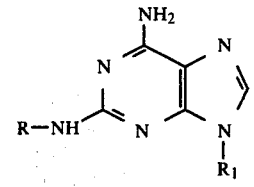

wherein
R is lower alkyl of 1 to 4 carbon atoms inclusive or cyclohexyl;
R$_1$ is cyclohexyl or 2-cyclohexenyl; or a pharmaceutically acceptable acid addition salt thereof.

2. The compound of claim 1 which is 9-(2-cyclohexenyl)-2-n-propylamino-9H-adenine or a pharmaceutically acceptable acid addition salt thereof.

3. The compound of claim 1 which is 9-(2-cyclohexenyl)-2-cyclohexylamino-9H-adenine or a pharmaceutically acceptable acid addition salt thereof.

4. The compound of claim 1 which is 9-cyclohexyl-2-n-propylamino-9H-adenine or a pharmaceutically acceptable acid addition salt thereof.

5. The compound of claim 1 which is 9-cyclohexyl-2-cyclohexylamino-9H-adenine or a pharamaceutically acceptable acid addition salt thereof.

* * * * *